US006770027B2

(12) United States Patent
Banik et al.

(10) Patent No.: US 6,770,027 B2
(45) Date of Patent: Aug. 3, 2004

(54) ROBOTIC ENDOSCOPE WITH WIRELESS INTERFACE

(75) Inventors: Michael S. Banik, Bolton, MA (US); Lucien Alfred Couvillon, Jr., Concord, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/177,491

(22) Filed: Jun. 21, 2002

(65) Prior Publication Data

US 2003/0069475 A1 Apr. 10, 2003

Related U.S. Application Data

(63) Continuation-in-part of application No. 09/971,419, filed on Oct. 5, 2001.

(51) Int. Cl.⁷ .............................................. A61B 1/005
(52) U.S. Cl. ...................... 600/146; 600/109; 600/117; 600/118; 600/145; 600/151; 600/152; 600/179; 348/65; 348/66; 348/67; 348/68; 348/69; 348/70; 348/71; 348/72; 348/73; 348/74
(58) Field of Search ................................. 600/109, 117, 600/118, 145, 146, 151, 152, 179; 348/65, 66, 67, 68, 69, 70, 71, 72, 73, 74

(56) References Cited

U.S. PATENT DOCUMENTS

| 4,273,111 A | 6/1981 | Tsukaya | 128/6 |
| 4,286,585 A | 9/1981 | Ogawa | 128/6 |

(List continued on next page.)

FOREIGN PATENT DOCUMENTS

| ES | 2 048 086 | 1/1992 | ............ H01B/1/12 |
| ES | 2 062 930 | 12/1992 | ............ H01B/1/12 |

(List continued on next page.)

OTHER PUBLICATIONS

John David Wyndham Madden, "Conducting Polymer Actuators," Massachusetts Institute of Technology, Sep. 2000.

(List continued on next page.)

*Primary Examiner*—John P. Leubecker
*Assistant Examiner*—Aaron Roane
(74) *Attorney, Agent, or Firm*—Mayer Fortkort & Williams, PC; David B. Bonham, Esq.

(57) ABSTRACT

An endoscope apparatus and method of operating the same. The endoscope apparatus comprises an endoscope portion and a control and display unit. The endoscope portion preferably comprises: (i) a sensor disposed at a distal end of the endoscope portion and providing endoscope data; (ii) one or more electronically controlled actuators (e.g., electroactive polymer actuators) controlling the operation of the endoscope portion based on received control signals; (iii) a first wireless transceiver coupled to the sensor and the one or more electronically controlled actuators, transmitting received endoscope data from the sensor and forwarding received control signals to the one or more electronically controlled actuators; and (iv) a portable power source (e.g., a battery) coupled to the sensor, the first wireless transceiver, and the one or more electronically controller actuators. The control and display unit preferably comprises: (i) a second wireless transceiver coupled via a wireless link to the first transceiver in the endoscope portion and receiving endoscope data from the first transceiver and transmitting control signals to the first transceiver; (ii) a control portion coupled to the second wireless transceiver and sending control signals to the one or more actuators in the endoscope portion via the first and second wireless transceivers; and (iii) a display portion that displays information received from the sensor via the first and second wireless transceivers. Another aspect of the present invention is directed to a method for providing single-use endoscopes to one or more hospitals.

29 Claims, 11 Drawing Sheets

U.S. PATENT DOCUMENTS

| | | | |
|---|---|---|---|
| 4,499,895 A | 2/1985 | Takayama | 128/6 |
| 4,503,842 A | 3/1985 | Takayama | 128/4 |
| 4,543,090 A | 9/1985 | McCoy | 604/95 |
| 4,601,705 A | 7/1986 | McCoy | 604/95 |
| 4,753,223 A | 6/1988 | Bremer | 128/4 |
| 4,790,624 A | 12/1988 | Van Hoye et al. | 350/96.26 |
| 4,832,473 A | 5/1989 | Ueda | 350/506 |
| 4,846,573 A | 7/1989 | Tayler et al. | 356/241 |
| 4,884,557 A | 12/1989 | Takehana et al. | 128/4 |
| 4,899,731 A | 2/1990 | Takayama et al. | 128/4 |
| 4,930,494 A | 6/1990 | Takehana et al. | 128/4 |
| 4,977,886 A | 12/1990 | Takehana et al. | 128/4 |
| 4,987,314 A | 1/1991 | Gotanda et al. | 250/551 |
| 5,090,956 A | 2/1992 | McCoy | 604/95 |
| 5,188,111 A | 2/1993 | Yates et al. | 128/657 |
| 5,239,982 A | 8/1993 | Trauthen | 128/4 |
| 5,250,167 A * | 10/1993 | Adolf et al. | 204/299 |
| 5,268,082 A | 12/1993 | Oguro et al. | 204/282 |
| 5,337,732 A | 8/1994 | Grundfest et al. | 128/4 |
| 5,347,987 A | 9/1994 | Feldstein et al. | 128/4 |
| 5,374,965 A * | 12/1994 | Kanno | 348/705 |
| 5,389,222 A | 2/1995 | Shahinpoor | 204/299.2 |
| 5,396,879 A | 3/1995 | Wilk et al. | 128/4 |
| 5,431,645 A | 7/1995 | Smith et al. | 606/1 |
| 5,482,029 A | 1/1996 | Sekiguchi et al. | 600/109 |
| 5,492,131 A | 2/1996 | Galel | 128/772 |
| 5,535,759 A * | 7/1996 | Wilk | 128/898 |
| 5,556,370 A | 9/1996 | Maynard | 600/151 |
| 5,556,700 A | 9/1996 | Kaneto et al. | 428/332 |
| 5,624,380 A | 4/1997 | Takayama et al. | 600/151 |
| 5,631,040 A | 5/1997 | Takuchi et al. | 427/100 |
| 5,645,520 A | 7/1997 | Nakamura et al. | 600/151 |
| 5,651,366 A | 7/1997 | Liang et al. | 128/662.06 |
| 5,662,587 A | 9/1997 | Grundfest et al. | 600/114 |
| 5,701,904 A * | 12/1997 | Simmons et al. | 128/670 |
| 5,771,902 A | 6/1998 | Lee et al. | 128/897 |
| 5,819,749 A | 10/1998 | Lee et al. | 128/899 |
| 5,855,565 A | 1/1999 | Bar-Cohen et al. | 604/104 |
| 5,857,962 A | 1/1999 | Bracci et al. | 600/105 |
| 5,871,439 A * | 2/1999 | Takahashi et al. | 600/118 |
| 5,873,817 A | 2/1999 | Kokish et al. | 600/143 |
| 5,878,159 A * | 3/1999 | Taleblou et al. | 382/128 |
| 5,906,591 A | 5/1999 | Dario et al. | 604/95 |
| 5,916,146 A | 6/1999 | Allotta et al. | 600/141 |
| 5,957,833 A | 9/1999 | Shan | 600/117 |
| 6,071,234 A | 6/2000 | Takada | 600/114 |
| 6,106,457 A * | 8/2000 | Perkins et al. | 600/175 |
| 6,109,852 A | 8/2000 | Shahinpoor et al. | 414/1 |
| 6,139,489 A * | 10/2000 | Wampler et al. | 600/109 |
| 6,162,171 A | 12/2000 | Ng et al. | 600/141 |
| 6,249,076 B1 * | 6/2001 | Madden et al. | 310/363 |
| 6,428,470 B1 * | 8/2002 | Thompson | 600/173 |
| 6,468,203 B2 * | 10/2002 | Belson | 600/146 |
| 6,514,237 B1 | 2/2003 | Maseda | 604/533 |
| 6,547,723 B1 * | 4/2003 | Ouchi | 600/146 |
| 6,554,765 B1 * | 4/2003 | Yarush et al. | 600/132 |
| 2002/0062062 A1 | 5/2002 | Belson et al. | 600/146 |

FOREIGN PATENT DOCUMENTS

| | | | | |
|---|---|---|---|---|
| JP | 3004830 | 1/1991 | | A61B/1/00 |
| JP | 03109021 | 5/1991 | | A61B/1/00 |
| JP | 03139325 | 6/1991 | | A61B/1/00 |
| JP | 3170125 | 7/1991 | | A61B/1/00 |
| JP | 05177002 | 7/1993 | | A61M/25/01 |
| JP | 05184531 | 7/1993 | | A61B/1/00 |
| JP | 07088788 | 4/1995 | | B25J/13/00 |
| JP | 07120684 | 5/1995 | | G02B/23/24 |
| JP | 08010336 | 1/1996 | | A61M/25/01 |
| JP | 8066351 | 3/1996 | | A61B/1/00 |
| JP | 8322783 | 12/1996 | | A61B/1/00 |
| JP | 08322786 | 12/1996 | | A61B/1/00 |
| JP | 10014863 | 1/1998 | | A61B/1/00 |
| JP | 11048171 | 2/1999 | | B25J/7/00 |
| JP | 2001096478 | 4/2001 | | B25J/5/00 |
| WO | WO 98/11816 | 2/1998 | | A61B/1/05 |
| WO | WO 01/58973 A2 | 8/2001 | | |

OTHER PUBLICATIONS

Active Endoscope (ELASTOR, Shape Memory Alloy Robot), http://mozu.mes.titech.ac.jp/research/medical/endscope/endscope.html, 9 pages including 3 figures and 4 photographs.

Koji Ikuta et al., "Shape Memory Alloy Servo Actuator System with Electric Resistance Feedback and Application for Active Endoscope," IEEE Int'l Conference on Robotics and Automation (Apr. 24–29, 1988), pp. 427–430.

David L. Brock, "Review of Artificial Muscle Based on Contractile Polymers," MIT Artificial Intelligence Laboratory, A.I. Memo No. 1330, Nov. 1991, pp. 1–12.

Yoseph Bar–Cohen, ed., Electroactive Polymer (EAP) Actuators as Artificial Muscles, SPIE Press (2001), Chapter 1, pp. 3–44.

Yoseph Bar–Cohen, ed., Electroactive Polymer (EAP) Actuators as Artificial Muscles, SPIE Press (2001), Chapter 7, pp. 193–221.

Kubler et al., "An Endoscopic Navigation System," Proceedings of Medicine Meets Virtual Reality—MMVR 2001, pp. 253–255.

Kubler et al., "Endoscopic Robots," Proceedings of 3rd International Conference on Medical Image Computing and Computer–Assisted Intervention—MICCAI 2000, pp. 949–955.

Worldwide ElectroActive Polymers (Artificial Muscles) Newsletter, vol. 3, No. 1 (Jun. 2001).

"Smart Catheters," from http://www.piaggio.ccii.unipi.it/cathe.htm, printed Aug. 27, 2001.

"Snake–like Flexible Micro–robot," from http://www.agip.sciences.univ–metz.fr/~mihalach/Copernicus_project_engl. html, Project start: May 1, 1995.

"Robot Snake with Flexible Real–Time Control," http://ais.gmd.de/BAR/snake.html, last updated 01–10–17.

Jager et al., "Microfabricating Conjugated Polymer Actuators," Science, vol. 290 (Nov. 24, 2000), pp. 1540–1545.

Electroactive Polymer (EAP) Actuators as Artificial Muscles, Yoseph Bar–Cohen, ed., SPIE Press (2001), Chapter 16, pp. 457–495.

Electroactive Polymer (EAP) Actuators as Artificial Muscles, Yoseph Bar–Cohen, ed., SPIE Press (2001), Chapter 21, pp. 615–659.

Yoseph Bar–Cohen, Smart Structures and Materials 2001: Electroactive Polymer Actuators and Devices, Yoseph Bar–Cohen, ed., Proceedings of SPIE, vol. 4329 (Mar. 5–8, 2001), pp. 1–6.

Madden et al., Smart Structures and Materials 2001: Electroactive Polymer Actuators and Devices, Yoseph Bar–Cohen, ed., Proceedings of SPIE, vol. 4329 (Mar. 5–8, 2001), pp. 72–83.

Pelrine et al., Smart Structures and Materials 2001: Electroactive Polymer Actuators nd Devices, Yoseph Bar–Cohen, ed., Proceedings of SPIE, vol. 4329 (Mar. 5–8, 2001), pp. 335–349.

Jeon et al., Smart Structures and Materials 2001: Electroactive Polymer Actuators and Devices, Yoseph Bar–Cohen, ed., Proceedings of SPIE, vol. 4329 (Mar. 5–8, 2001), pp. 380–388.

Cho et al., Smart Structures and Materials 2001: Electroactive Polymer Actuators and Devices, Yoseph Bar–Cohen, ed., Proceedings of SPIE, vol. 4329 (Mar. 5–8, 2001), pp. 466–474.

Charles J. Lightdale, MD, "New Developments in Endoscopy," American College of Gastroenterology 65th Annual Scientific Meeting, Oct. 16, 2000, pp. 1–9.

G. Zuccaro, "Procedural Sedation in the GI Suite," 16th Annual Meeting 2001: May 3–6, 2001.

Piers et al., "Miniature Parallel Manipulators for Integration in a Self–propelling Endoscope," IUAP P4/24 IMechS Workshop, Oct. 27, 1999.

"Walking machines: 0–legged–robots," compiled by C. Duntgen, Aug. 26, 2000.

Jae–Do Nam, "Electroactive Polymer (EAP) Actuators and Devices for Micro–Robot Systems" Nov. 28, 2000.

"Snake–like Robot Endoscopes," from http://robby.Caltech.edu/~chen/res–medical.html, page updated Aug. 14, 1996.

Alberto Mazzoldi et al., "Conductive Polymer Based Structures for a Steerable Catheter," *Smart Structures and Materials 2000: Electroactive Polymer Actuators and Devices*, Yoseph Bar–Cohen, ed., Proceedings of SPIE, vol. 3987 (2000), pp. 273–280.

A. Brett Slatkin et al., "The Development of a Robotic Endoscope," *Proceedings of the 1995 IEEE/RSJ International Conference on Intelligent Robots and Systems: Human Robot Interaction and Cooperative Robots*, vol. 2, Aug. 5, 1995, pp. 162–171.

A. Della Santa et al., "Intravascular Microcatheters Steered by Conducting Polymer Actuators," Proceedings of the 18$^{th}$ Annual International Conference of the IEEE Engineering in Medicine and Biology Society, vol. 5, 1997, pp. 2203–2204.

* cited by examiner

ROBOTIC ENDOSCOPE WITH WIRELESS INTERFACE

STATEMENT OF RELATED APPLICATION

This application is a continuation-in-part of U.S. Ser. No. 09/971,419, filed Oct. 5, 2001 and entitled "Robotic Endoscope."

FIELD OF THE INVENTION

The present invention relates to robotic endoscopes, and more particularly to robotic endoscopes that are adapted for remote control.

BACKGROUND OF THE INVENTION

Diagnostic endoscopy is a common procedure in the United States and other countries, perhaps being second only to interventional cardiology in generating hospital revenue.

Traditional endoscopy typically utilizes flexible endoscopes that are steered by internal tension wires. These probes typically include means for illumination, lavage, and imaging (usually with a CCD camera chip at the distal tip), as well as a working channel through which, for example, biopsy forceps, snares, and fulguration probes can be introduced. Such devices allow physicians to see and treat polyps and other common disorders of the alimentary, gastrointestinal, and respiratory tracts.

Even after 20 years of refinement, present day endoscopes for gastroenterology are complex and costly. Furthermore, hospitals must keep a large inventory of endoscopes on hand, ready for use. Moreover, the endoscopes are typically washed and disinfected, by hand labor and in expensive washing machines. As a result, gastroenterology departments in hospitals must dedicate substantial capital investment to endoscopes and consoles, and significant staff time and floor space to the storage and reprocessing of endoscopes. Reduction in the need for endoscope inventory, testing, preparation and handling would free up hospital resources that could be applied to cost savings or increased patient throughput.

SUMMARY OF THE INVENTION

The above disadvantages of present day endoscopes are addressed by the present invention. According to a first aspect of the present invention, an endoscope apparatus is provided, which comprises an endoscope portion and a control and display unit.

The endoscope portion preferably comprises: (i) a sensor disposed at a distal end of the endoscope portion and providing endoscope data; (ii) one or more electronically controlled actuators (e.g., electroactive polymer actuators) controlling the operation of the endoscope portion based on received control signals; (iii) a first wireless transceiver coupled to the sensor and the one or more electronically controlled actuators, transmitting received endoscope data from the sensor and forwarding received control signals to the one or more electronically controlled actuators; and (iv) a portable power source (e.g., a battery) coupled to the sensor, the first wireless transceiver, and the one or more electronically controller actuators.

The control and display unit preferably comprises: (i) a second wireless transceiver coupled via a wireless link to the first transceiver in the endoscope portion and receiving endoscope data from the first transceiver and transmitting control signals to the first transceiver; (ii) a control portion coupled to the second wireless transceiver and sending control signals to the one or more actuators in the endoscope portion via the first and second wireless transceivers; and (iii) a display portion that displays information received from the sensor via the first and second wireless transceivers.

The electronically controlled actuators are preferably electroactive polymer actuators, as such actuators favor single use economies.

The control and display unit beneficially includes a personal computer, such as a desktop or laptop computer, due to the low cost and ready availability of the same.

In some embodiments, the control portion further comprises a manual steering device that converts manual movements into the control signals that are sent to the actuators via the first and second wireless transceivers. One example of such a manual steering device is a joystick.

The sensor preferably includes an energy source, typically a light source such as a light emitting diode, and an imaging detector, typically a camera such as a CMOS camera.

In some embodiments, the endoscope portion further comprises a control handle that is operable by a user. The control handle is disposed at a proximal end of the endoscope portion and is preferably integrated into the endoscope at the proximal end. The portable power source and the wireless interface can be disposed within the control handle, if desired.

In some embodiments, the endoscope apparatus further includes a remote server that is coupled to the control and display unit. For example, the control and display unit can further comprise a network access device such as a modem to access the remote server over a network. The remote server can be adapted to perform a number of functions, including endoscope inventory tracking, diagnostic assistance and patient scheduling.

The remote server can contain, for example, a database of endoscope inventory data, patient data and examination images.

In certain embodiments, the first transceiver automatically communicates identifying data relating to the endoscope portion to the control and display unit, for example, to assist with setup, initialization of parameters, and calibration of a particular endoscope within a product family, and endoscope inventory tracking.

According to another aspect of the invention, a method of examining a body lumen is provided. In the method, an operator is provided with an endoscope apparatus like that above, whereupon the operator inserts the endoscope portion into a body lumen while controlling the shape of the endoscope portion using the control portion of the control and display unit. The body lumen is examined using the sensor of the endoscope portion. After inserting the endoscope portion and examining the body lumen, the operator can conduct a surgical procedure if desired.

Where the control and display unit of the endoscope apparatus is coupled to a remote server, the remote server can be used, for example, to track endoscope inventory, to perform patient scheduling, to access patient data and images stored within a database associated with the remote server, and to integrate the examination with the medical resources of local in-hospital intranets or the Internet.

According to another aspect of the present invention, a method for providing single-use endoscopes to one or more hospitals is provided. This method comprises: (a) detecting an identifier associated with each single use endoscope at one or more hospitals (using, for example, the above embodiment where the first transceiver automatically communicates identifying data to the control and display unit); (b) sending the identified single use endoscope information to a central server along with information regarding scheduled procedures; (c) determining single use endoscope future requirements at one or more hospitals based on the scheduled procedures and the identified single use endoscope information; (d) forwarding the single use endoscope future requirements to a manufacturing facility that manufactures the single use endoscopes; and (e) scheduling a manufacturing operation and a shipping operation to supply the single use endoscope future requirements to the one or more hospitals prior to inventory depletion.

The advantages of the present invention are numerous and include a reduction in endoscope inventory as well as a reduction (or elimination) of employee time, equipment, and floor space required for endoscope preparation and handling.

These and other embodiments and advantages of the present invention will become apparent from the following detailed description, and the accompanying drawings, which illustrate by way of example the features of the invention.

DETAILED DESCRIPTION OF THE INVENTION

Figure 14:
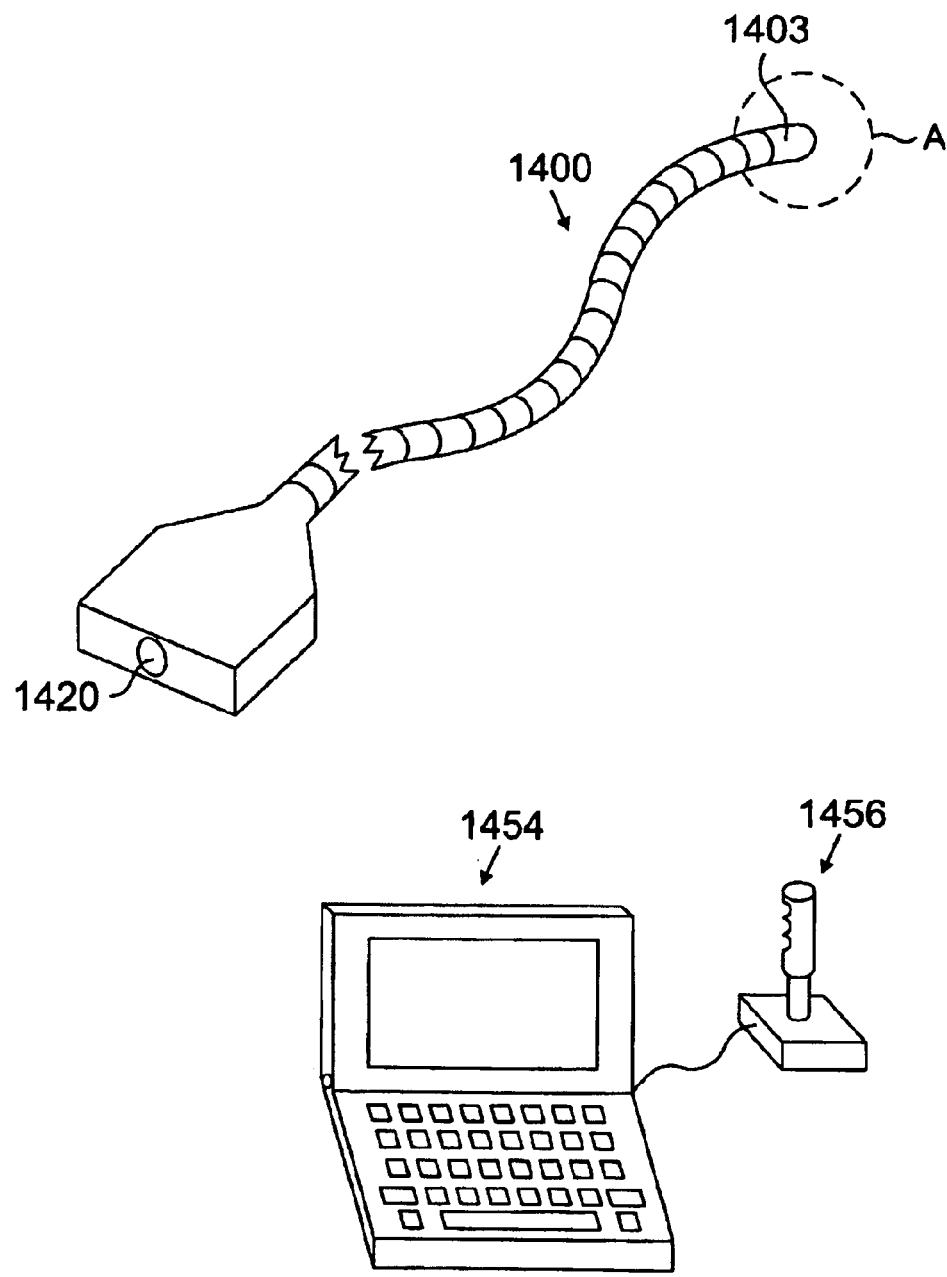
FIG. 14 is a schematic drawing of an endoscopic apparatus in accordance with the present invention.

Referring now to FIG. 14, according to a preferred embodiment of the invention, an endoscope portion 1400 is constructed as an elongated body that contains numerous electronic actuators (not illustrated), which are controlled by a control and display unit such as a computer 1454.

Figure 11:
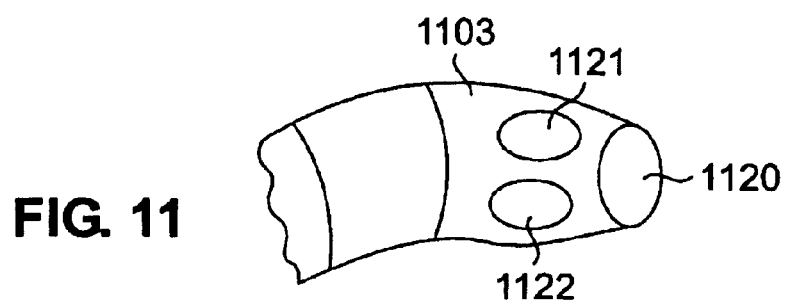
FIG. 11 is a schematic perspective view of the distal end of an endoscope in accordance with the present invention.

The working tip 1403 of the endoscope portion 1400, which is encircled by area A in FIG. 14 and is illustrated in more detail in FIG. 11, has a sensing system that senses the body lumen. More specifically, referring now to FIG. 11, the particular working tip 1103 illustrated has a sensing system that includes an energy source 1121 (e.g., a light source) and an imaging subsystem 1122 (e.g., an imaging detector such as a camera). A working channel 1120 is also illustrated in FIG. 11.

Referring again to FIG. 14, a power source (not shown), a wireless interface including drivers (not shown), and a working channel 1420 are provided at the proximal end of the endoscope portion 1400. The wireless interface of the endoscope portion communicates with a companion wireless interface within a remote computer 1454, which acts as a data and image management station. A steering system that includes a joystick 1456 is used in this particular embodiment.

The endoscopic systems of the present invention preferably utilize low cost systems components to achieve single-use economics. For example, as noted above, the endoscopes of the present invention preferably utilize wireless interface chipsets, rather than resorting to expensive, and frequently unreliable, electrical connectors. Inexpensive wireless interfaces are presently available from a number of sources, including Bluetooth™ wireless interfaces available from Motorola as well as IEEE 802.11b wireless interfaces available, for example, from Cisco, Apple and Lucent. Depending on the economics, a wireless interface can be provided, for example, for each module within the endoscope portion, or even for each actuator of the endoscope portion.

The sensing system used in the endoscope portion preferably comprises an energy source and an imaging subsystem (also referred to herein as an "imaging detector") at or near its distal end. For example, the energy source can be a light source such as a light emitting diode (e.g., a white-light-emitting laser diode) or a fiber optic light source, such as a bundle of optical fibers with a diffuser at the distal end, with light emitting diodes being presently preferred. The imaging system can be, for example, an optical fiber or a camera, such as CCD camera chip or CMOS camera chip. Low-cost CMOS or flying-spot imaging subsystems are presently preferred and are available from a number of sources, including Micron Photobit (Pasadena, Calif.), Conexant (Newport Beach, Calif.), CByond (Oak Park, Calif.), Microvision (Bothell, Wash.), Micromedical (Castle Pines Village, Colo.), Photon Vision Systems (Cortland, N.Y.), Sarnoff Laboratories (Princeton, N.J.), Vanguard Labs (Taiwan) and many other vendors.

Of course, other light-based and non-light-based systems are possible, operating in the visible or other regions of the spectrum, using reflected radiation or fluorescence, sensing endogenous or exogenous (e.g., contrast-agent dye induced) responses, or including other imaging modalities like ultrasound or optical coherence tomography.

The endoscopes of the present invention generally have a familiar external appearance. For example, the endoscopes are preferably provided with one or more working channels that extend down the length of the endoscope portion, allowing, for example, for insufflation, lavage, and the introduction of tools such as biopsy forceps, snares, and fulguration probes. However, as discussed in more detail below, the endoscopes of the present invention preferably use low-cost electronic actuators made from electroactive polymer, which are integrated into the endoscope structure, instead using conventional pull wires (sometimes referred to as Bowden cables). Although simple pull-wire or stylet systems, which are known in the art, can be used in connection with the present invention so long as they have favorable manufacturing economics, electroactive polymer actuators are presently superior in this respect. Moreover, electroactive actuators can provide additional benefits in controlling the shape and stiffness of the endoscope portion along its length, as will become clear from the discussion below.

The power source for the endoscopes of the present invention is typically a battery. By building battery power into the endoscope, interconnection cost and complexity are reduced. Moreover, a built-in limit on re-use can be provided, if desired, for example, to limit endoscope use to a single patient and thereby avoid cross-contamination issues.

One or more batteries can be provided essentially anywhere within the endoscope, but are preferably provided at the proximal end of the endoscope, which can be, for example, in the form of an integrated, sealed control handle. The electronics for the wireless interface, including drivers for the electronic actuators and other components, can also be provided at the proximal end of the endoscope.

A companion control and display unit is preferably a computer, such as a standard laptop personal computer, which provides processing, memory and display capacity, and is also equipped with a companion wireless interface and suitable operating software. If desired, a computer mouse pad, a built-in or peripheral joystick, or an analogous device may be used to steer and control the endoscope, for example, manually or with semi-automatic assistance based on image analysis as discussed in more detail below.

The laptop is preferably connected to the Internet, for example, via network, dial-up or wireless connection. Once the computer is web-enabled, images and patient studies can be stored, analyzed, retrieved, and shared in one or more remote databases. The wireless connection between the endoscope and laptop can optionally provide for automatic recognition, by the computer, of the endoscope model, configuration, serial number, calibration, and other data. Integration of this automatic recognition feature with a web-based inventory and patient-scheduling management system allows for automatic management of inventory, re-ordering and just-in-time delivery, reducing inventory and handling costs. If desired, a user prompt can suggest and confirm re-orders.

The endoscope is typically delivered in a sterile package. Once the endoscope is removed from the package, it can be powered on, for example, by (a) bringing it close to the computer, which automatically recognizes its proximity and turns it on, (b) manually engaging a small sealed power-on switch, (c) using a switch-wand key, which may be included on the endoscope, and so forth. If desired, a welcome screen can be set up to ask for logon and patient information. The user then typically controls the endoscope, performs the examination (for example, selecting images and video sequences for storage and annotation during the examination), completes the examination, and logs out.

Figure 13:
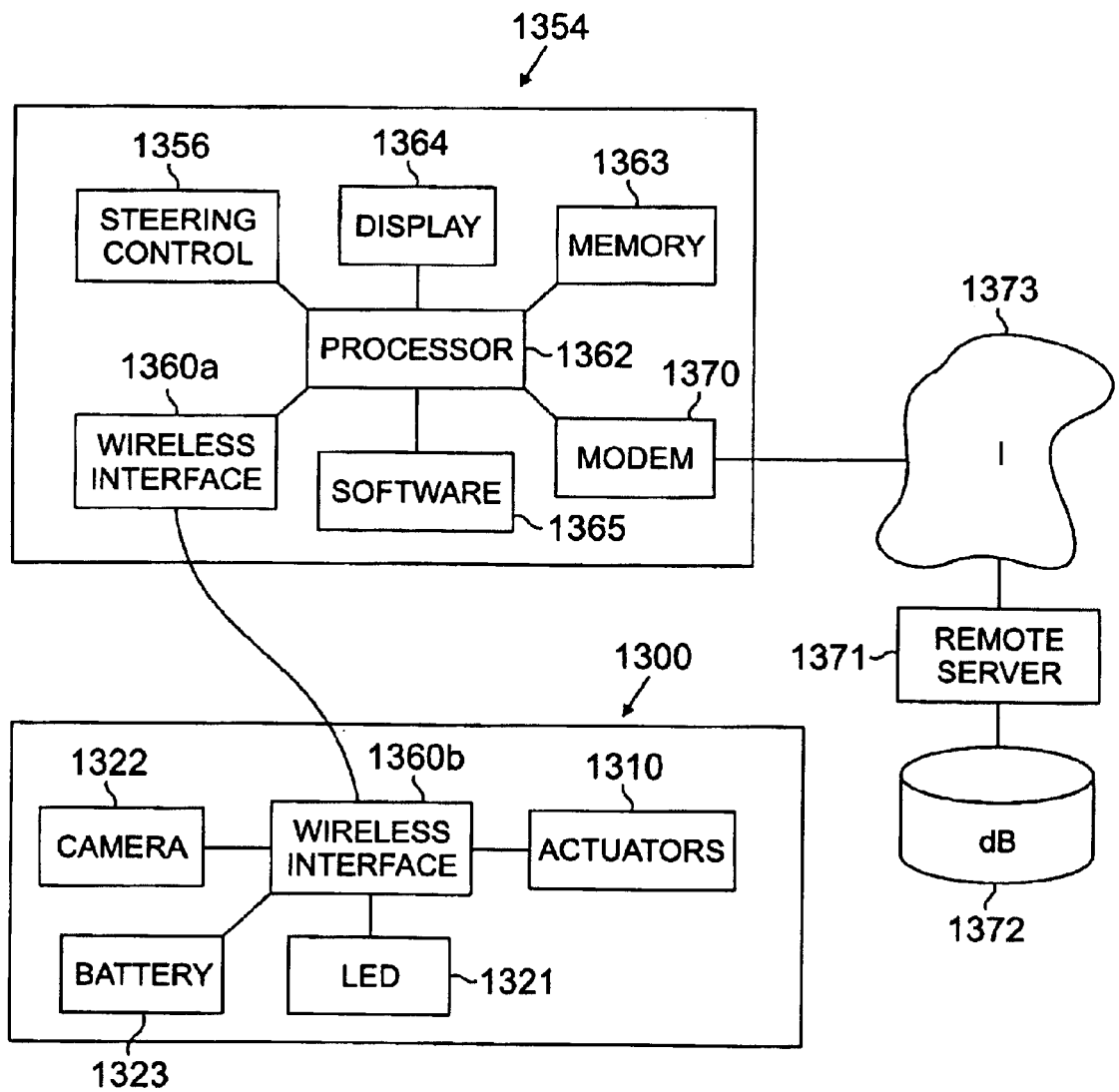
FIG. 13 depicts an exemplary embodiment of an endoscope apparatus, according to an embodiment of the present invention, in block diagram format.

One specific embodiment of an endoscope apparatus of the invention is presented in block diagram format in FIG. 13. The endoscopic system shown includes an endoscope portion 1300 and a control and display unit such as a computer 1354. The endoscope portion is powered by battery 1323. A wireless interface 1360a and 1360b (including drivers) is provided between the endoscope 1300 and the computer 1354. Control signals are sent from the computer 1354 to the endoscope portion 1300 via the wireless interface 1360a, 1360b. The control signals include those that are ultimately sent from drivers associated with the electronic interface 1360b to the actuators 1310, but can also include other signals, for example, signals to an LED 1321 and camera 1322 at the distal end of the endoscope 1300. At the same time, data is also sent from the endoscope portion 1300 to the computer 1354 via the wireless interface 1360a, 1360b, including imaging data from the camera 1322 as well as data from strain gauges, depth gauges, etc. (not shown) if present.

As is typical, the computer 1354 contains a processor 1362, memory 1363 and display 1364. Camera data transmitted over the wireless interface 1360a, 1360b is shown on the display 1364. Using this information, the operator can operate the steering control 1356, which outputs data that are used (along with any other relevant data, such as data from strain gauges, etc.) by the operating software 1365 to calculate a control signal. The control signal is sent to the actuators 1310 in the endoscope 1300 via drivers in the wireless interface 1360b to steer and control the shape of the endoscope portion 1300.

In the embodiment illustrated, the laptop is connected to a remote server 1371 via modem 1370 and the Internet 1373, allowing, for example, for images and patient studies to be stored, retrieved, analyzed and shared in one or more remote databases 1372.

Figure 15:
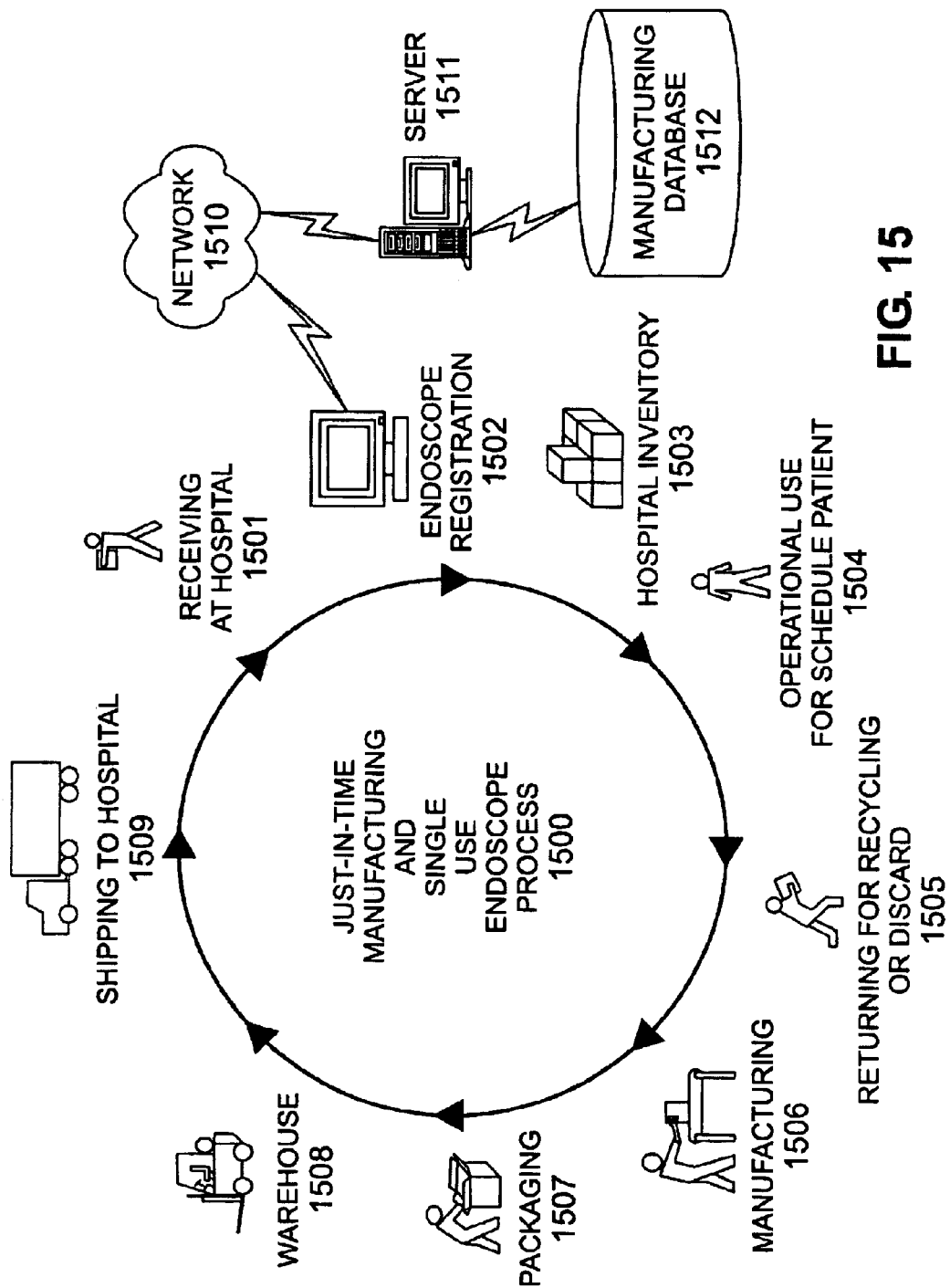
FIG. 15 illustrates a method for providing endoscopes for use in a hospital, according to an embodiment of the present invention.

Turning now to FIG. 15, according to another aspect of the present invention, a method 1500 for providing endoscopes for use in a hospital is disclosed. This method 1500 enables a hospital to control costs associated with endoscopes, both the acquisition costs as well as the costs associated with allocation of hospital resources, such as floor space for inventory, cleaning rooms for sterilization of previously used endoscopes, and personnel resources allocated to performing these functions. The method 1500 of the present invention includes a single use endoscope, as described above, that avoids the costs associated with sterilization and re-use, as well as a wireless interface with a web-enabled personal computer 1502 that provides inventory control and manufacturing scheduling so that just-in-time delivery mechanisms can be employed to reduce inventory size, and thereby save the costs associated with inventory size. Thus, the continuing process 1500 can be thought of as beginning with delivery of a particular endoscope to the hospital 1501. As described above, the endoscope is a single-use device that comes packaged in a sterile container. The endoscope in its container is then brought in close proximity to the web-enabled personal computer or workstation 1502. The wireless interface between the computer and the endoscope can operate through the packaging. This enables the computer to register the endoscope by serial number in a database 1512 to which the computer 1502 is coupled over a network 1510, such as the Internet. The database 1512 maintains records of manufacturing date, patient information, total hospital inventory, other scheduled operations involving endoscopes, and so forth. If desired, the endoscope database 1512 can be connected to a hospital information system (hosptital database), allowing integration of patient records, patient image databases, scans in other modalities, laboratory data, and so forth. As part of the registration process 1502, a particular patient operation 1504 is associated with the newly received endoscope. This includes the date of projected use. Once the device is registered, the device is placed in the hospital inventory 1503, which can be much smaller and therefore less costly on a per unit basis. After using the single-use endoscope in the operation 1504, the endoscope can be discarded in a hospital waste container, or returned to the manufacturing for recycling 1505. By comparing the scheduled uses of the endoscope at the hospital, the network computer (e.g., server 1511) and database 1512 can determine replacement needs, including dates when the replacements will be required. The database 1512 and associated server 1511 will determine manufacturing requirements based on the replacement needs. These manufacturing requirements are aggregated with the needs of other hospital to schedule manufacturing levels in the manufacturing process 1506. As the units are received from the manufacturing process 1506, they are then packaged 1507, stored in a warehouse inventory 1508, and then shipped directly to the hospitals 1509 for which they were manufactured. This reduces inventory costs at both the manufacturer and the hospital, thereby reducing the costs associated with the endoscope. The units then arrive just-in-time prior to the scheduled operations at the various hospitals.

The endoscope portion will now be described in more detail. In a preferred embodiment of the invention, as the endoscope portion is advanced, the actuators are preferably controlled such that the overall shape of the elongated body of the endoscope portion in 3-dimensional space reflects the natural (i.e., unstressed) shape of the lumen into which the endoscope portion is inserted, minimizing stress on the lumen. The endoscope portion follows the natural trajectory of the organ being examined. It is as if a wave, corresponding to the natural shape of the organ, travels along the endoscope portion as it is advanced, so that contact with, and stress upon, the lumenal walls, is minimized.

The actuators used in connection with the endoscopes of the present invention are electrically controlled actuators (as used herein, "electrically controlled actuators" include those actuators that are activated by photons) such as piezoelectric activators, shape memory activators and/or electroactive polymer actuators.

Actuators based on electroactive polymers, members of a family of plastics referred to as "conducting polymers," are preferred. Electroactive polymers are a class of polymers characterized by their ability to change shape in response to electrical stimulation. They typically structurally feature a conjugated backbone and have the ability to increase electrical conductivity under oxidation or reduction. Some common electroactive polymers are polyaniline, polypyrrole and polyacetylene. Polypyrrole is pictured below:

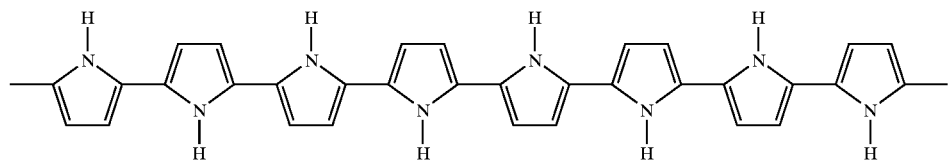

These materials are typically semi-conductors in their pure form. However, upon oxidation or reduction of the polymer, conductivity is increased. The oxidation or reduction leads to a charge imbalance that, in turn, results in a flow of ions into the material in order to balance charge. These ions, or dopants, enter the polymer from an ionically conductive electrolyte medium that is coupled to the polymer surface. The electrolyte may be a gel, a solid, or a liquid. If ions are already present in the polymer when it is oxidized or reduced, they may exit the polymer.

It is well known that dimensional changes may be effectuated in certain conducting polymers by the mass transfer of ions into or out of the polymer. For example, in some conducting polymers, the expansion is due to ion insertion between chains, whereas in others interchain repulsion is the dominant effect. Thus, the mass transfer of ions both into and out of the material leads to an expansion or contraction of the polymer.

Currently, linear and volumetric dimensional changes on the order of 25% are possible. The stress arising from the dimensional change can be on the order of 3 MPa, far exceeding that exerted by smooth muscle cells.

Figure 1:
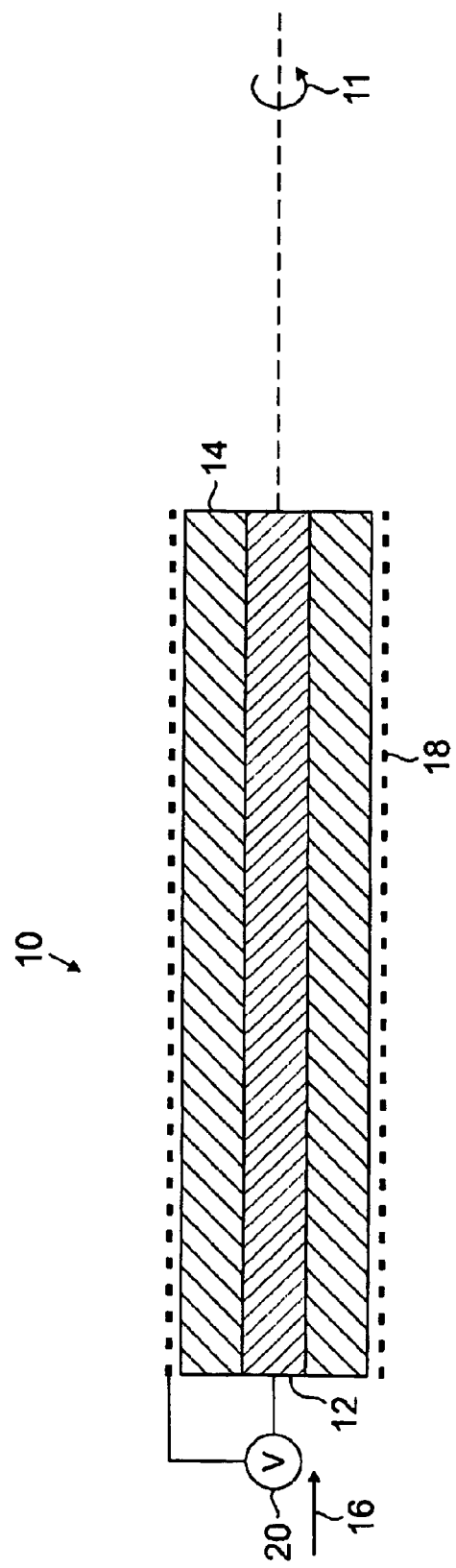
FIG. 1 is a schematic diagram of an actuator useful in connection with the present invention.

Referring now to FIG. 1, an actuator 10 is shown schematically in cross-section. Active member 12 of actuator 10 has a surface coupled with electrolyte 14 and has an axis 11. Active member 12 includes a conducting polymer that contracts or expands in response to the flow of ions out of, or into, the active member 12. Ions are provided by electrolyte 14, which adjoins member 12 over at least a portion, and up to the entirety, of the surface of active member 12 in order to allow for the flow of ions between the two media. Many geometries are available for the relative disposition of member 12 and electrolyte 14. In accordance with preferred embodiments of the invention, member 12 may be a film, a fiber or a group of fibers, or a combination of multiple films and fibers disposed so as to act in consort for applying a tensile force in a longitudinal direction substantially along axis 11. The fibers may be bundled or distributed within the electrolyte 14.

Active member 12 includes an electroactive polymer. Many electroactive polymers having desirable tensile properties are known to persons skilled in the art. In accordance with preferred embodiments of the invention, active member 12 is a polypyrrole film. Such a polypyrrole film may be synthesized by electrodeposition according to the method described by M. Yamaura et al., "Enhancement of Electrical Conductivity of Polypyrrole Film by Stretching: Counter-ion Effect," Synthetic Metals, vol. 36, pp.209–224 (1988), which is incorporated herein by reference. In addition to polypyrrole, any conducting polymer that exhibits contractile or expansile properties may be used within the scope of the invention. Polyaniline and polysulfone are examples of two such conducting polymers.

Electrolyte 14 may be a liquid, a gel, or a solid, so long as ion movement is allowed. Moreover, where the electrolyte 14 is a solid, it should move with the active member 12 and should not be subject to delamination. Where the electrolyte 14 is a gel, for example, it may be an agar or polymethylmethacrylate (PMMA) gel containing a salt dopant. Counter electrode 18 is in electrical contact with electrolyte 14 in order to provide a return path for charge to source 20 of potential difference between member 12 and electrolyte 14. Counter electrode 18 may be any electrical conductor, for example, another conducting polymer, a conducting polymer gel, or a metal such as gold, which can be applied by electroplating, chemical deposition, or printing. In order to activate actuator 10, a current is passed between active member 12 and counter electrode 18, inducing contraction or expansion of member 12. Additionally, the actuator may have a flexible skin for separating the electrolyte from an ambient environment.

Additional information regarding the construction of actuators, their design considerations, and the materials and components that may be employed therein, can be found, for example, in U.S. Pat. No. 6,249,076, assigned to Massachusetts Institute of Technology, and in Proceedings of the SPIE, Vol. 4329 (2001) entitled "Smart Structures and Materials 2001: Electroactive Polymer and Actuator Devices (see, in particular, Madden et al, "Polypyrrole actuators: modeling and performance," at pp. 72–83), both of which are hereby incorporated by reference in their entirety.

In general, as part of a failsafe mechanism for the devices of the present invention, it is beneficial that the actuators that are selected be of a type that relaxes in the event that power is interrupted.

The actuators can be disposed within the endoscopes of the present invention in a number of ways. For example, the actuators can be separately manufactured and subsequently attached to structural elements of the endoscopes. Alternatively, multiple actuators or actuator arrays can be disposed upon a sheet of material, for example, a polymeric sheet, which is associated with the endoscope.

Figure 2:
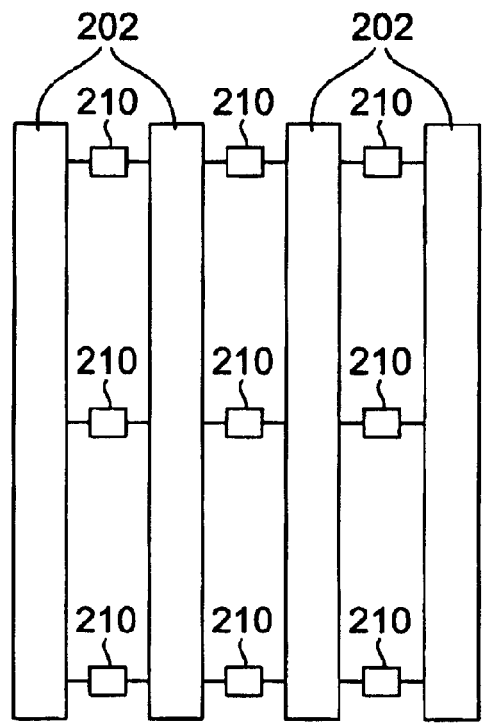
FIGS. 2–3 are schematic diagrams depicting some possible choices for the deployment of actuators with respect to the structural elements in the endoscopes of the present invention.

FIG. 2 illustrates one possible configuration of actuators and structural elements in accordance with the present invention, it being understood that the number of actuators and structural elements, as well as the spatial disposition of these elements with respect to one another, can vary widely from one embodiment to another. In the particular embodiment depicted, a series of four annular structural elements 202 are illustrated, with three actuators 210 disposed between each pair of structural elements 202.

In general, the shape of the endoscopes of the present invention can be inferred from the intrinsic position-dependent electrical properties of the electroactive polymer. However, if desired, a number of sensors, such as strain gauges, can be employed to provide electronic feedback concerning the orientation of the actuators and structural elements within the assembly. This electronic feedback will also provide a number of additional advantages, including compensation for physiologic changes, greater stability, error correction, and immunity from drift. Strain gauges suitable for use in the present invention include (a) feedback electroactive polymer elements whose impedance or resistance varies as a function of the amount of strain in the device and (b) conventional strain gauges in which the resistance of the device varies as a function of the amount of strain in the device, thus allowing the amount of strain to be readily quantified and monitored. Such strain gauges are commercially from a number of different sources, including National Instruments Co., Austin, Tex., and include piezoresistive strain gauges (for which resistance varies nonlinearly with strain) and bonded metallic strain gauges (for which resistance typically varies linearly with strain). The later strain gauges consist of very fine wire or metallic foil that is arranged in a grid pattern. The grid is bonded to a thin backing or carrier, which may be directly attached to the substrate being monitored for strain. Consequently, the strain experienced by the substrate is transferred directly to the strain gauge, which responds with a change in electrical resistance. Commercially available strain gauges typically have nominal resistance values within the range of 30 to 3000Ω, with 120Ω, 350Ω and 1000Ω devices being especially common.

The assembly is preferably further provided with a restoring force that biases the entire assembly toward a substantially linear configuration (although one skilled in the art will appreciate that the assembly may also be biased toward a non-linear configuration). In such an embodiment, the actuators may be used to deviate from this substantially linear configuration. A number of mechanisms can be provided to impart a suitable bias to the assembly. For example, the assembly can be inserted within an elastic sleeve (not shown), which tends to restore the system into a substantially linear configuration whenever any distorting forces applied by the actuators are not present. As one alternative, a series of springs (not shown) or other suitably elastic members can be disposed between the structural elements to restore the assembly to a substantially linear configuration. As another alternative, the structural elements within the assembly can be sufficiently elastic to restore the assembly to a substantially linear configuration. Once a biasing force is provided, the assembly can be bent into a number of configurations by simply contracting one or more of the actuators disposed between the various structural elements.

Figure 3:
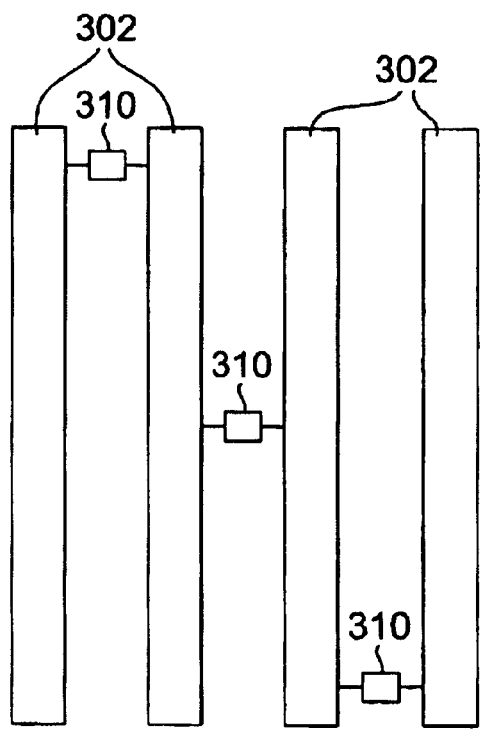

While the assembly depicted in FIG. 2 has the actuators disposed along three parallel axes, numerous variations based upon the above noted considerations are possible. For example, the actuators 310 between structural elements 302 can be deployed in a staggered arrangement as illustrated in FIG. 3.

Moreover, rather than providing the assembly with a biasing force that restores the entire assembly to a biased (e.g., substantially linear) configuration, a series of pivot points can be provided between the structural elements, if desired. In this way, the assembly can be bent into the desired configuration by placing at least two actuators in tension with one another. Hence, the actuators in a system of this type operate on a principle similar to the operation of skeletal muscles in living organisms such as snakes.

Figure 4:
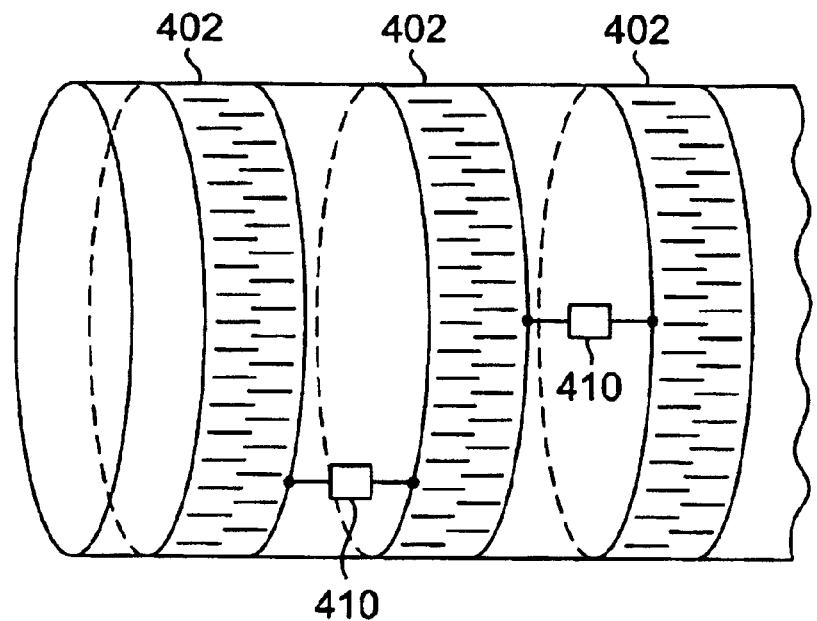
FIGS. 4–5 are schematic perspective views of structural elements and actuators useful in the endoscopes of the present invention.

Moreover, a number of configurations and variations are possible with respect to the structural elements. For example, while the structural elements are depicted in FIGS. 2–4 as a series of closed loops, the structural elements can also include open loops, akin to the vertebrae structure of a snake. Moreover, the loops can be replaced by tubes of various lengths if desired. For example, a series of short tubes constructed in a fashion similar to known vascular, biliary or esophageal stents can be used. Such a structure is illustrated in FIG. 4, in which a plurality of actuators 410 is positioned between a series of short stent-like elements 402.

The structural elements may also be combined into a unitary structure. Thus, for example, the discrete loops in some of the embodiments described above may be replaced by a single helical structural element, with the actuators deployed between adjacent turns of the helix. It is to be noted, however, that the adjacent turns of the helix act very much like the series of discrete loops depicted, for example, in FIG. 3.

Figure 5:
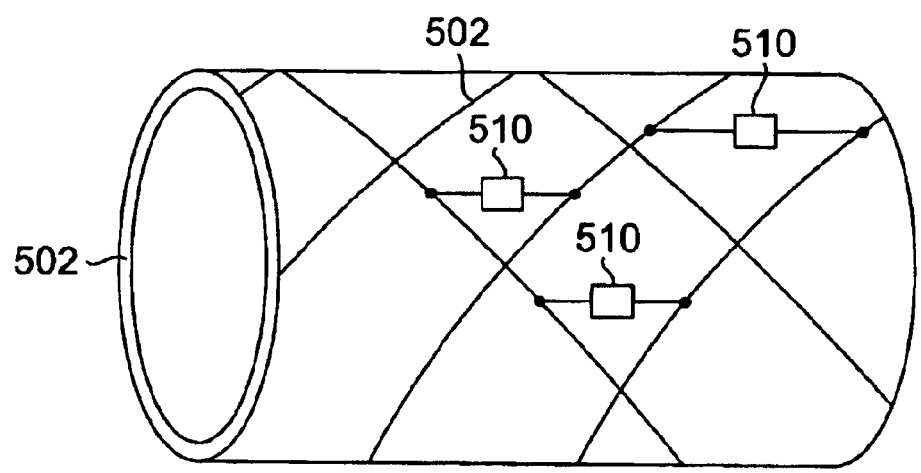

In other instances, a single elongated tube can be used as a structural element. As above, the designs for such structures can be in the form of stent-like elements. For example, referring to FIG. 5, actuators 510 can be disposed between adjacent members of a mesh structure 502. If a flexible or elastic material is used in the construction, the mesh structure 502 can be configured so that it will possess an inherent bias or memory that acts to restore the assembly to its original (e.g., substantially linear) configuration. The actuators 502 can then be used to deflect the structure from this configuration as needed to reflect the natural shape of the lumen into which the endoscope is inserted. Of course, a source of bias such as an elastic sleeve (shown here as being inserted within the mesh structure 502) can also be provided if desired.

Figure 6A:
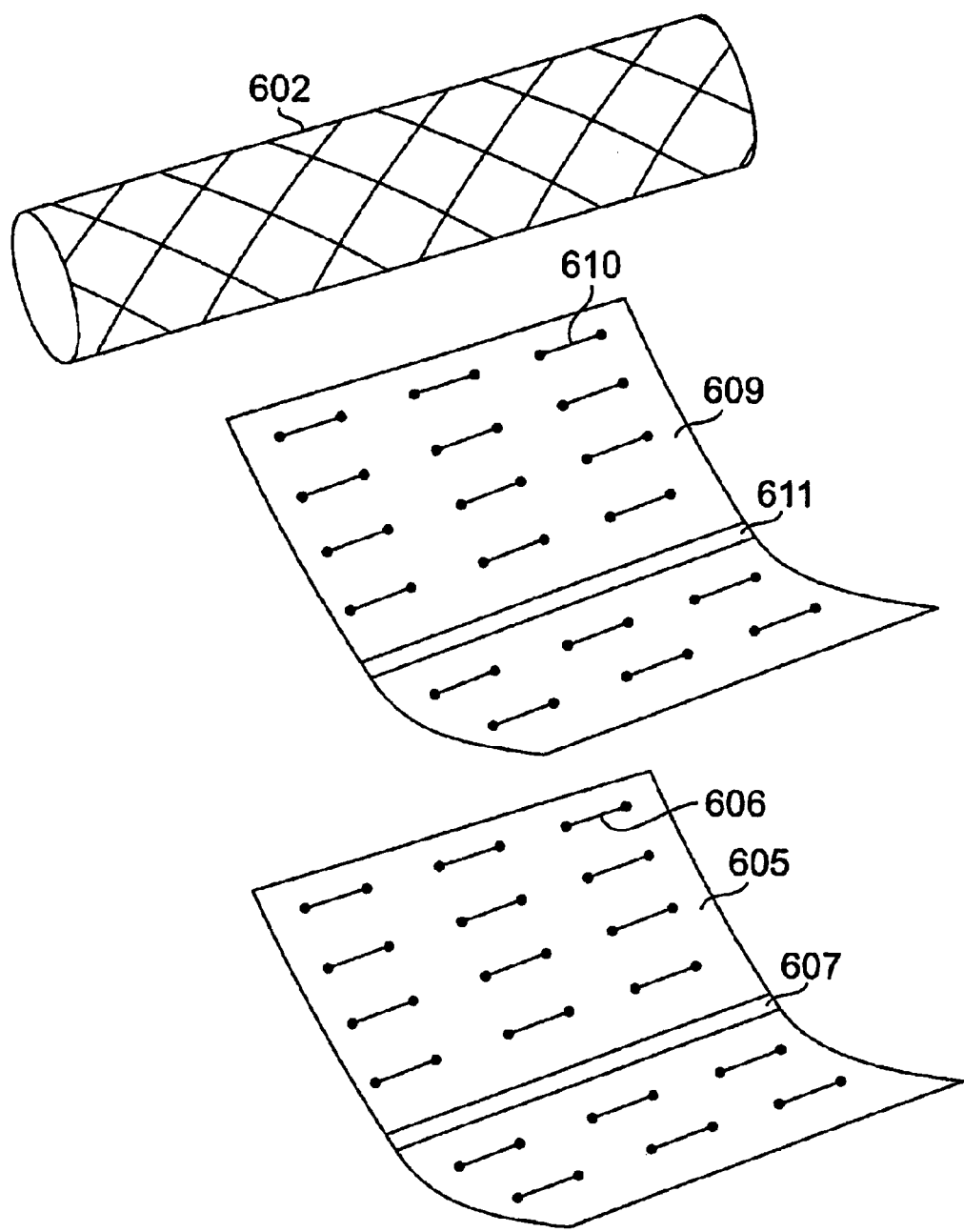
FIGS. 6A–B are schematic perspective views of a structural element and associated components, which are disposed on sheets, useful in the endoscopes of the present invention.

In the embodiments described above, the actuators are directly coupled to the structural elements. However, this need not be the case as illustrated, for example, in FIGS. 6A and 6B. FIG. 6A illustrates a structural element 602 which includes a wire mesh, and two flexible sheets 605 and 609. A series of actuators 610 (a single actuator is numbered) is printed on one sheet 609, along with a control bus 611 for transmitting control signals to the actuators 610 from a controlling device (individual interconnections with actuators 610 are not illustrated). A plurality of strain gauges or feedback polymer elements 606 (a single strain gauge is numbered) is printed on the other sheet 605, along with a readout bus 607 for transmitting information from the strain gauges 606 (individual interconnections with strain gauges 606 are not illustrated) to a controlling device.

Preferably, the two sheets employed in the structural element comprise elastomeric materials such as, for example, styrene-butadiene copolymers, polychloroprene, nitrile rubber, butyl rubber, polysulfide rubber, cis-1,4-polyisoprene, ethylene propylene terpolymers, silicone rubber, or polyurethane rubber. Alternatively the sheets may be constructed from stiffer polymers like those used in electronic printed circuits or cables, such as polyimide (e.g., Kapton®), and relieved by selective cutting, e.g. with a laser, to provide the appropriate flexibility.

Figure 6B:
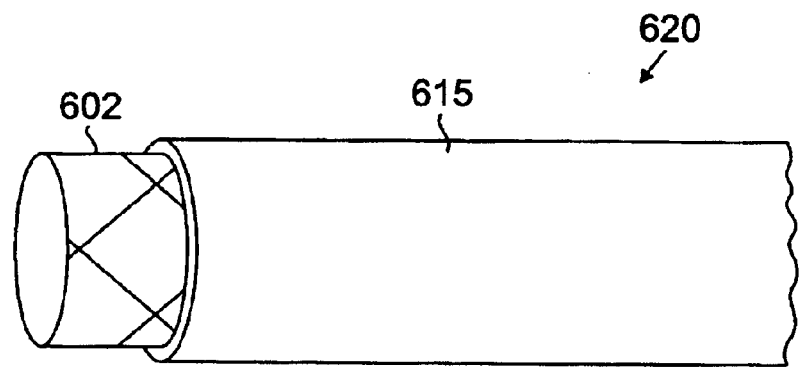

The sheets are registered with one another and the layers are bonded together to form a unitary mass using suitable means as are known to the art. Such means may include, for example, lamination, spot welding, interlayer electrical connections similar to the plated-through holes of multiplayer printed circuits, the use of an adhesive layer or a tie layer, and so forth. The bonded structure 615 is then wrapped around the structural element 602, and the edges are joined to provide a cylindrical assembly 620 as illustrated in FIG. 6B. A protective sheath may be disposed over the assembly, if desired. In this design, the structural element 602, the bonded structure 615 or both will act to bias the overall assembly 620 in a preferred configuration, which will typically be a linear configuration. The actuators 610 are used to deflect this structure to the desired degree, while the strain gauges 606 provide feedback regarding the extent of the deflection.

Figure 7:
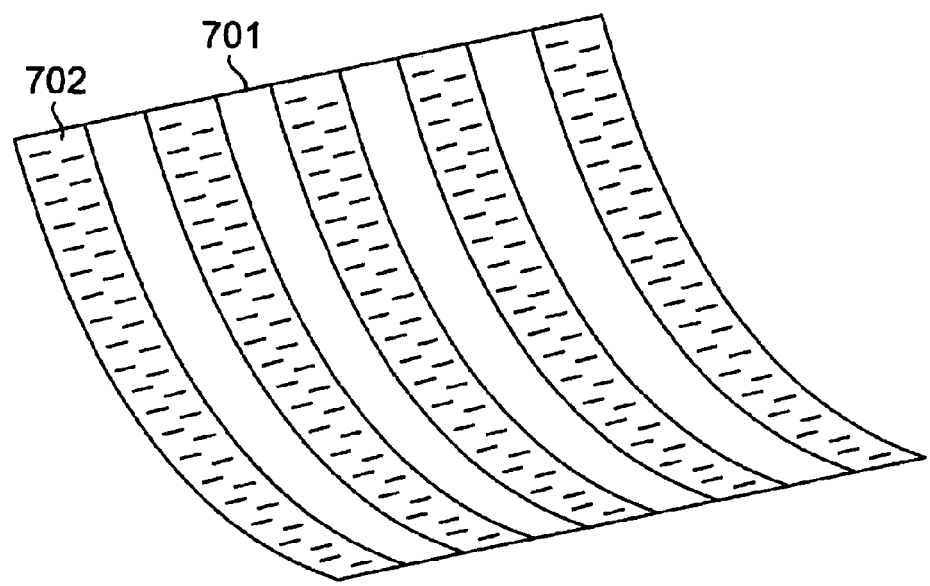
FIG. 7 is a schematic perspective view of a sheet with structural elements incorporated therein, in accordance with an embodiment of the present invention.

If desired, the structural elements, as well as the strain gauges 606 and actuators 610, can also be provided in the form of a printed sheet. For example, FIG. 7 illustrates sheet 701 having printed thereon a series of relatively stiff structural elements 702 which, when rolled up, will form structural elements similar to those illustrated in FIG. 4.

Figure 8A:
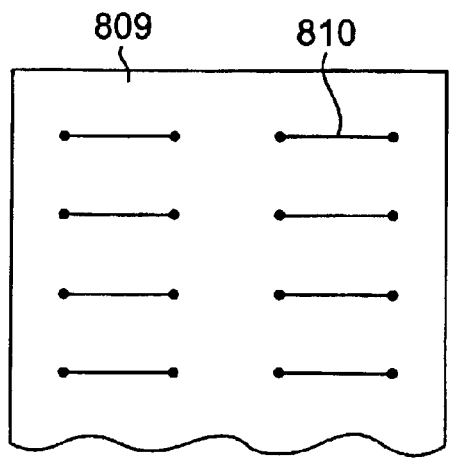
FIGS. 8A–C are schematic top views illustrating some possible orientations of actuators on a substrate, in accordance with an embodiment of the present invention.
Figure 8B:
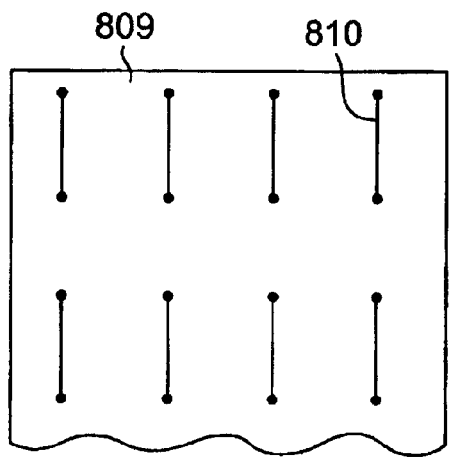
Figure 8C:
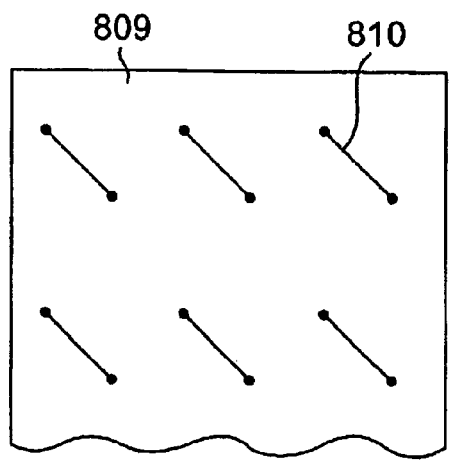

In general, the actuators are oriented in the direction needed for control, somewhat like the muscles of a snake. For example, FIGS. 8A, 8B and 8C illustrate three sheets 809, each having a series of actuators 810 (one actuator is numbered in each figure), which are oriented in various directions. By laminating these sheets together, a laminated structure (not shown) can be created which can bend, contract circumferentially, and so forth.

Each actuator and strain gauge within the endoscopes of the present invention is preferably in communication with, and is individually controllable by (e.g., using drivers within the above mentioned electric interface) a controlling device. This allows these elements to be monitored/driven for the purpose of effecting changes to the configuration of the overall device.

The actuators and strain gauges may be in direct communication with the controlling device (wireless interface, for example) by means of dedicated circuits linking each of these elements to the device. However, it is more preferred to deploy these elements in an array in which each element is in communication with the controlling device by means of a common communications cable. The signals from each element may be digital or analog. If need be, digital-to-analog or analog-to-digital converters may be provided to convert the signals from one format to the other.

The signals from each element may be conveniently managed and transmitted over the common cable by multiplexing. Multiplexing schemes that may be used for this purpose include frequency-division multiplexing, wave-division multiplexing, or time-division multiplexing. Suitable multiplexers and demultiplexers can be employed at each end of the cable and along its length at the position of each actuator or gage.

In terms of electronic data storage, each actuator and strain gauge may be given a separate address in electronic memory where information concerning the state of the element is stored. This information may be accessed to determine the state of the device, or for the purpose of performing operations on the device or its elements. The memory in which the information is stored may be of a volatile or non-volatile type, and may be in the device itself, but is preferably in a remote control and display unit (e.g., laptop computer). Thus, for example, if there are 16 actuators and 16 strain gauges in each module and 256 modules in the entire endoscope, then there will be 256×32 or $2^{13}$ addresses. These components can thus be addressed using, for example, a 16-bit bus or cable and a decoder.

Numerous cable configurations are possible. For example, the cables can be directly connected to the actuators. Alternatively, the cables can be printed onto a sheet, in which case each flat sheet upon which the actuators (and strain gauges, if desired) are printed may be similar to a flexible printed circuit board in that the necessary elements are printed upon a flexible substrate. Each layer can be provided with its own track wires and control cables (e.g., the readout and control buses discussed above). Alternatively, the actuators and strain gauges can be connected to a separate interconnect layer, for example, by plated through-holes or vias (these also function as "rivets" to hold the composite together). These through-holes can tie into a series of conductive track wires disposed on the interconnect layer, which track wires connect to a "spinal cord", such as a cable bundle, flat cable or ribbon cable that runs the length of the device.

The endoscope portions of the present invention are typically provided with a slippery, lubricious coating to assist in its advancement into the lumen of interest. Lubricious coatings are known in the art and include, without limitation, hydrogel coatings, silicones, and fluoropolymers such as polytetrafluoroethylene.

The endoscopes of the present invention are also provided with features that are common to traditional endoscopes. For example, the endoscope portions can be provided with channels for lavage (e.g., a tube for saline delivery) and insufflation (e.g., a tube for expending carbon dioxide). Moreover, a working channel is typically provided, which extends through the elongated body and allows surgical instruments used in conventional endoscopes to be advanced to distal end (as well as channels for lavage and insufflation, if not otherwise provided within the device). Such surgical instruments include biopsy probes (e.g., snares or baskets), biopsy forceps, and electrosurgery probes (e.g., fulguration probes for RF ablation).

Any number of techniques can be used to advance the endoscope into the body lumen of the patient, which is typically a vertebrate animal, and preferably a human. For example, the endoscope can be manually inserted as is the practice with traditional endoscopes. The manual insertion can either be direct (e.g., by means of a control handle) or by operation of a manual drive mechanism (e.g., by operation of a crank). The endoscope may also be advanced by a drive mechanism (e.g., an electric servo payout motor) using a drive algorithm. The preferred techniques of the present invention, however, do not involve any form of internal anchoring, which could cause discomfort in the individual to be examined.

The distance of endoscope advancement may be monitored in accordance with the present invention. Numerous methods can be used for this purpose. For instance, various depth gauges or linear displacement transducers can be used. As one example, a depth gauge can be supplied, which contains a rotating gear wheel whose revolutions are monitored. As another example, a linear displacement transducer containing a depth code which can be read optically (using, for example, bar-codes and an optical source and detector) or magnetically (using, for example, a magnetic code and a Hall effect sensor) can be used to determine the extent of endoscope advancement. These and numerous other known methods are available for determining advancement distance.

Figure 9:
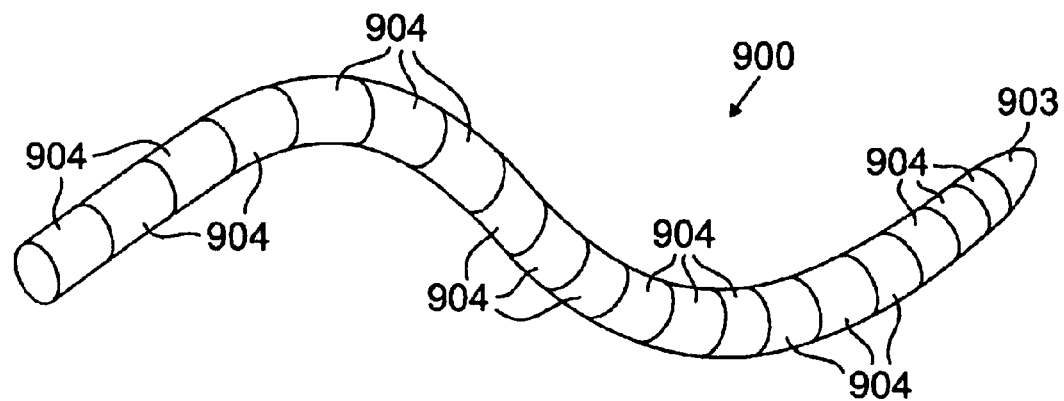
FIG. 9 is a schematic perspective view of the body portion of an endoscope in accordance with the present invention.
Figure 10:
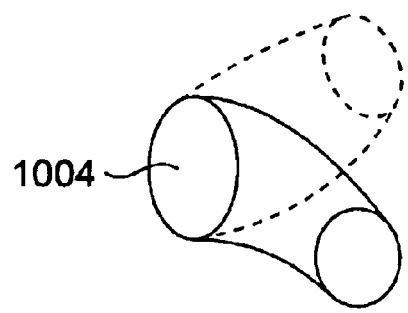
FIG. 10 is a schematic perspective view of an endoscope module in accordance with the present invention.

The endoscopes of the present invention are preferably divided into a series of "deflection modules", each of which includes a plurality of actuators that allow the module to take on a variety of shapes in 3-dimensional space in response to input by the control device. The greater the number of modules, the finer the control of the 3-dimenisonal orientation of the endoscope. A simplified schematic diagram of an endoscope 900 with eighteen modules 904 and a working tip 903 is found in FIG. 9. The overall shape of the endoscope is established by manipulating the deflection of each of the modules. As illustrated in FIG. 10, the actuators can be activated to deflect a given module 1004 from a first position (designated by solid lines) to a second position (designated by dashed lines). As one specific example, a module can consist of a group of actuators between two or more structural elements as discussed above, allowing the module to be bent in an up, down, left or right fashion. Of course, myriad other options are available. Additional degrees of freedom in deflection are also possible, e.g., changes in diameter for expansion or contraction, as might be used to deliver stents; or changes in length, as might be used for propulsion or access.

The curvature of each module is typically modified by the voltage that is applied to each actuator. As noted above, the endoscope is preferably provided with a plurality of strain gauges that provide a sensing function for electronic feedback. This electronic feedback will provide a number of advantages, including greater stability, error correction, and immunity from drift. More preferably, a strain gauge is provided for each actuator in the endoscope. To the extent that the behavior of the actuator in response to an electronic input is highly predictable, however, electronic feedback will not be necessary.

As noted above, the endoscope is preferably provided with a steering system, which is used to control electronic actuators in a working tip (also referred to herein as the "lead module") of the endoscope. A number of options are available for carrying out this task. For example, the endoscope can be provided with a manual steering system that is operated under image guidance. For example, electrical control from the computer can be based on manual steering input using a joystick or the like. The joystick or the like is manipulated by an operator based on an image provided from the distal end of the endoscope. The operator will typically endeavor to maintain the lead module at the center of the body lumen.

As another example, based on input from a sensing system like that discussed above, electrical control can be provided by means of a edge-tracking or center-seeking algorithm to keep the distal end of the endoscope at the center of the body lumen.

In many preferred embodiments, the endoscope will be steered in a semiautomatic fashion, for example, using a computer algorithm like that discussed above to suggest a direction of travel, with a trained operator acting to either accept or reject the computer-generated suggestion. In this instance, it may be desirable to tailor the algorithm to reflect operator preferences based upon operator profiles, which can include examination histories and databases, preferably web-enabled as discussed above.

Once a position of interest is reached, the working tip applies specific diagnostic or therapeutic functions, just as in conventional endoscopy.

As the endoscope is advanced into the body lumen, a 3-dimensional representation the desired shape of the endoscope can be stored into memory, with further data being added with increasing depth of insertion.

According to one preferred embodiment, the orientation of the lead module as a function of advancement distance is stored to the computer, acting as a map for subsequent deflection modules. The distance data can be provided, for example, from a depth gauge or linear displacement transducer as described above. The data relating to the orientation of the lead module can be provided, for example, using input from a steering step (e.g., input from a joystick or input from a center-seeking computer algorithm) or from position sensors or strain gauges. Using this map, electrical control signals for the actuators are calculated as a function of insertion depth. As a result, as subsequent modules arrive at the position that was previously occupied by the lead module, the actuators within these modules are operated such that they take the orientation of the lead module when it was present at that particular depth of insertion.

Figure 12A:
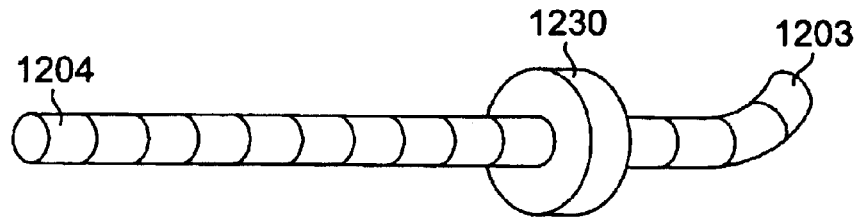
FIGS. 12A–C are schematic perspective views illustrating the ability of the endoscopes of the present invention to retain their orientation at a given depth of insertion.
Figure 12B:
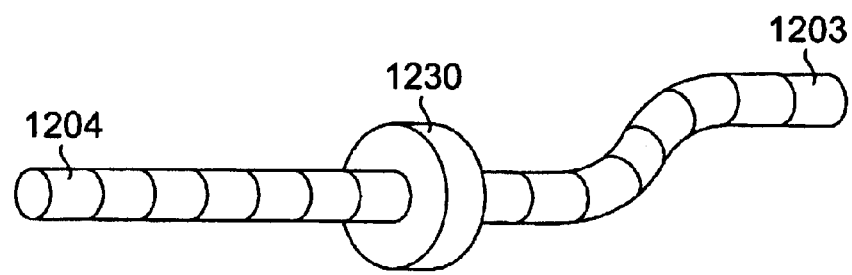
Figure 12C:
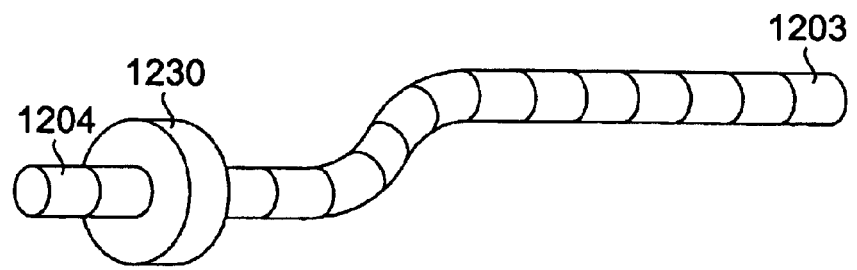

The result of the above is that the endoscope retains its path in 3-dimensional space, reflecting the shape of the tract (trajectory) that it travels through. This is illustrated in FIGS. 12A–12C, which contain a simplified schematic diagram of an endoscope, consisting of a number of deflection modules 1204 (one numbered) and a working tip 1203, as well as a linear displacement transducer 1230, which is provided, for example, at the point of insertion. These figures illustrate the orientation of the endoscope: shortly after insertion (FIG. 12A), at an intermediate point of insertion (FIG. 12B) and at a point of full insertion (FIG. 12C). As seen from these figures, as it advances, the endoscope retains its orientation at a given depth of insertion.

Although the present invention has been described with respect to several exemplary embodiments, there are many other variations of the above-described embodiments that will be apparent to those skilled in the art, even where elements have not explicitly been designated as exemplary. It is understood that these modifications are within the teaching of the present invention, which is to be limited only by the claims appended hereto.

What is claimed is:

1. A method of examining a body lumen comprising:
providing an operator with an endoscope apparatus, said endoscope apparatus comprising: (a) an endoscope portion, which further comprises: (i) a sensor disposed at a distal end of said endoscope portion and providing endoscope data; (ii) one or more electronically controlled actuators controlling operation of the endoscope portion based on received control signals; (iii) a first wireless transceiver coupled to the sensor and the one or more electronically controlled actuators, transmitting received endoscope data from the sensor and forwarding received control signals to the one or more electronically controlled actuators; and (iv) a portable power source coupled to the sensor, the first wireless transceiver, and the one or more electronically controller actuators; and (b) a control and display unit comprising: (i) a second wireless transceiver coupled via a wireless link to the first transceiver in said endoscope portion and receiving endoscope data from the first transceiver and transmitting control signals to the first transceiver; (ii) a control portion coupled to the second wireless transceiver and sending control signals to the one or more actuators in the endoscope portion via said first and second wireless transceivers; and (iii) a display portion that displays information received from said sensor via said first and second wireless transceivers;
inserting said endoscope portion of said endoscope apparatus into a body lumen while controlling the shape of said endoscope portion using said control portion; and
examining said body lumen using said sensor of said endoscope portion,
wherein said endoscope apparatus further comprises a remote server coupled to the control and display unit, and
wherein said remote server is adapted to track endoscope inventory.

2. The method of claim 1, wherein said portable power source comprises a battery.

3. The method of claim 1, wherein said control and display unit comprises a personal computer.

4. The method of claim 1, wherein said control portion further comprises a manual steering device converting manual movements into the control signals to be sent to the one or more actuators via the first and second wireless transceivers.

5. The method of claim 4, wherein said steering device comprises a joystick.

6. The method of claim 1, wherein said sensor comprises an energy source outputting energy and an imaging detector detecting reflected energy.

7. The method of claim 6, wherein said energy source comprises a light source.

8. The method of claim 7, wherein said light source comprises a light emitting diode.

9. The method of claim 6, wherein said imaging detector comprises a camera.

10. The method of claim 9, wherein said camera comprises a CMOS camera.

11. The method of claim 1, wherein said endoscope portion further comprises a working channel.

12. The method of claim 1, wherein said endoscope portion further comprises a control handle operable by a user, disposed at a proximal end of said endoscope portion, and integrated into said endoscope portion at said proximal end.

13. The method of claim 12, wherein said portable power source and said wireless interface are disposed within said control handle.

14. The method of claim 1, wherein said control and display unit further comprises a network access device to access said remote server over a network.

15. The method of claim 14, wherein said network access device comprises a modem.

16. The method of claim 1, wherein said remote server is further adapted to perform patient scheduling.

17. The method of claim 1, wherein said remote server comprises a database of patient data and examination images.

18. The method of claim 1, wherein said first transceiver communicates identifying data for said endoscope portion automatically to said control and display unit.

19. The method of claim 1, further comprising conducting a surgical procedure within said lumen using said endoscope apparatus.

20. The method of claim 1, wherein said endoscope portion is a single use endoscope portion, and wherein said method further comprises disposing of said endoscope portion after use.

21. A method of examining a body lumen comprising:
providing an operator with an endoscope apparatus, said endoscope apparatus comprising: (a) an endoscope portion, which further comprises: (i) a sensor disposed at a distal end of said endoscope portion and providing endoscope data; (ii) one or more electronically controlled actuators controlling operation of the endoscope portion based on received control signals; (iii) a first wireless transceiver coupled to the sensor and the one or more electronically controlled actuators, transmitting received endoscope data from the sensor and forwarding received control signals to the one or more electronically controlled actuators; and (iv) a portable power source coupled to the sensor, the first wireless transceiver, and the one or more electronically controller actuators; and (b) a control and display unit comprising: (i) a second wireless transceiver coupled via a wireless link to the first transceiver in said endoscope portion and receiving endoscope data from the first transceiver and transmitting control signals to the first transceiver; (ii) a control portion coupled to the second wireless transceiver and sending control signals to the one or more actuators in the endoscope portion via said first and second wireless transceivers; and (iii) a display portion that displays information received from said sensor via said first and second wireless transceivers;
inserting said endoscope portion of said endoscope apparatus into a body lumen while controlling the shape of said endoscope portion using said control portion; and
examining said body lumen using said sensor of said endoscope portion,
wherein said endoscope apparatus further comprises a remote server coupled to the control and display unit, and
wherein said remote server is adapted to perform patient scheduling.

22. The method of claim 21, wherein said control and display unit comprises a personal computer.

23. The method of claim 21, wherein said control portion further comprises a manual steering device converting manual movements by an operator to control signals for said one or more actuators, wherein said operator operates said manual steering device to control said actuators.

24. The method of claim 21, wherein said sensor comprises a light source and a camera.

25. The method of claim 21, wherein said remote server further comprises a database and said remote server is adapted to access patient data and images stored within said database.

26. The method of claim 21, wherein data identifying said endoscope portion is automatically sent from said endoscope portion to said control and display unit.

27. The method of claim 21, wherein said endoscope portion is a single use endoscope portion, and wherein said method further comprises disposing of said endoscope portion after use.

28. A method of examining a body lumen comprising:

providing an operator with an endoscope apparatus, said endoscope apparatus comprising: (a) an endoscope portion, which further comprises: (i) a sensor disposed at a distal end of said endoscope portion and providing endoscope data: (ii) a plurality of electronically controlled, electroactive polymer actuators, said actuators controlling the shape of the endoscope portion in 3-dimensional space based on received control signals; (iii) a first wireless transceiver coupled to the sensor and the one or more electronically controlled actuators, transmitting received endoscope data from the sensor and forwarding received control signals to the one or more electronically controlled actuators; and (iv) a portable power source coupled to the sensor, the first wireless transceiver, and the one or more electronically controller actuators; and (b) a control and display unit comprising: (i) a second wireless transceiver coupled via a wireless link to the first transceiver in said endoscope portion and receiving endoscope data from the first transceiver and transmitting control signals to the first transceiver: (ii) a control portion coupled to the second wireless transceiver and sending control signals to the one or more actuators in the endoscope portion via said first and second wireless transceivers; and (iii) a display portion that displays information received from said sensor via said first and second wireless transceivers;

inserting said endoscope portion of said endoscope apparatus into a body lumen while controlling the shape of said endoscope portion using said control portion; and examining said body lumen using said sensor of said endoscope portion, wherein said endoscope apparatus further comprises a remote server coupled to the control and display unit and wherein said remote server is adapted to track endoscope portion inventory.

29. A method of examining a body lumen comprising:

providing an operator with an endoscope apparatus, said endoscope apparatus comprising: (a) an endoscope portion, which further comprises: (i) a sensor disposed at a distal end of said endoscope portion and providing endoscope data: (ii) a plurality of electronically controlled, electroactive polymer actuators, said actuators controlling the shape of the endoscope portion in 3-dimensional space based on received control signals; (iii) a first wireless transceiver coupled to the sensor and the one or more electronically controlled actuators, transmitting received endoscope data from the sensor and forwarding received control signals to the one or more electronically controlled actuators; and (iv) a portable power source coupled to the sensor, the first wireless transceiver, and the one or more electronically controller actuators; and (b) a control and display unit comprising: (i) a second wireless transceiver coupled via a wireless link to the first transceiver in said endoscope portion and receiving endoscope data from the first transceiver and transmitting control signals to the first transceiver: (ii) a control portion coupled to the second wireless transceiver and sending control signals to the one or more actuators in the endoscope portion via said first and second wireless transceivers; and (iii) a display portion that displays information received from said sensor via said first and second wireless transceivers;

inserting said endoscope portion of said endoscope apparatus into a body lumen while controlling the shape of said endoscope portion using said control portion; and examining said body lumen using said sensor of said endoscope portion, wherein said endoscope apparatus further comprises a remote server coupled to the control and display unit and wherein said remote server is adapted to perform patient scheduling.

* * * * *

UNITED STATES PATENT AND TRADEMARK OFFICE
CERTIFICATE OF CORRECTION

PATENT NO. : 6,770,027 B2
DATED : August 3, 2004
INVENTOR(S) : Michael S. Banik et al.

It is certified that error appears in the above-identified patent and that said Letters Patent is hereby corrected as shown below:

<u>Title page,</u>
Item [57], ABSTRACT,
Line 15, before "actuators," change "contoller" to -- controlled --.

<u>Column 1,</u>
Line 62, after "electronically", change "controller" to -- controlled --.

<u>Column 7,</u>
Line 14, after "other", change "hospital" to -- hospitals --.

<u>Column 9,</u>
Line 57, after "commercially," insert -- available --.

<u>Column 11,</u>
Line 37, change "known to the art" to -- known in the art --.
Line 39, change "multiplayer" to -- multilayer --.

<u>Column 12,</u>
Line 23, change last word "gage" to -- gauge --

<u>Column 13,</u>
Line 3, before "distal" insert -- the --.

<u>Column 15,</u>
Lines 22-23, after "electronically", change "controller" to -- controlled --.

<u>Column 16,</u>
Lines 43-44, after "electornically", change "controller" to -- controlled --.

<u>Column 17,</u>
Line 35, change first word "controller" to -- controlled --.

UNITED STATES PATENT AND TRADEMARK OFFICE
CERTIFICATE OF CORRECTION

PATENT NO. : 6,770,027 B2
DATED : August 3, 2004
INVENTOR(S) : Michael S. Banik et al.

It is certified that error appears in the above-identified patent and that said Letters Patent is hereby corrected as shown below:

Column 18,
Line 26, change first word "controller" to -- controlled --.

Signed and Sealed this

Twenty-eighth Day of December, 2004

JON W. DUDAS
*Director of the United States Patent and Trademark Office*

UNITED STATES PATENT AND TRADEMARK OFFICE
CERTIFICATE OF CORRECTION

PATENT NO.     : 6,770,027 B2
DATED          : August 3, 2004
INVENTOR(S)    : Michael S. Banik et al.

It is certified that error appears in the above-identified patent and that said Letters Patent is hereby corrected as shown below:

Title page,
Item [57], ABSTRACT,
Line 15, before "actuators," change "contoller" to -- controlled --.

Column 1,
Line 62, after "electronically", change "controller" to -- controlled --.

Column 7,
Line 14, after "other", change "hospital" to -- hospitals --.

Column 9,
Line 57, after "commercially," insert -- available --.

Column 11,
Line 37, change "known to the art" to -- known in the art --.
Line 39, change "multiplayer" to -- multilayer --.

Column 12,
Line 23, change last word "gage" to -- gauge --

Column 13,
Line 3, before "distal" insert -- the --.

Column 15,
Lines 22-23, after "electronically", change "controller" to -- controlled --.

Column 16,
Lines 43-44, after "electronically", change "controller" to -- controlled --.

Column 17,
Line 35, change first word "controller" to -- controlled --.

UNITED STATES PATENT AND TRADEMARK OFFICE
CERTIFICATE OF CORRECTION

PATENT NO. : 6,770,027 B2
DATED : August 3, 2004
INVENTOR(S) : Michael S. Banik et al.

It is certified that error appears in the above-identified patent and that said Letters Patent is hereby corrected as shown below:

Column 18,
Line 26, change first word "controller" to -- controlled --.

This certificate supersedes Certificate of Correction issued December 28, 2004.

Signed and Sealed this

Twenty-ninth Day of March, 2005

JON W. DUDAS
*Director of the United States Patent and Trademark Office*